(12) United States Patent
Shaw

(10) Patent No.: US 10,446,264 B2
(45) Date of Patent: Oct. 15, 2019

(54) SYSTEMS AND METHODS FOR MEDICAL DATA PROCESSING AND ANALYSIS

(71) Applicant: Attomarker Limited, Exeter (GB)

(72) Inventor: Andrew Mark Shaw, Exeter (GB)

(73) Assignee: Attomarker Limited, Exeter (GB)

( * ) Notice: Subject to any disclaimer, the term of this patent is extended or adjusted under 35 U.S.C. 154(b) by 895 days.

(21) Appl. No.: 14/764,557

(22) PCT Filed: Jan. 30, 2014

(86) PCT No.: PCT/GB2014/050240
§ 371 (c)(1),
(2) Date: Jul. 29, 2015

(87) PCT Pub. No.: WO2014/118536
PCT Pub. Date: Aug. 7, 2014

(65) Prior Publication Data
US 2015/0363560 A1     Dec. 17, 2015

(30) Foreign Application Priority Data

Jan. 30, 2013 (GB) .................................. 1301611.8

(51) Int. Cl.
*G16H 10/60* (2018.01)
*G16H 50/50* (2018.01)
*G16B 20/00* (2019.01)

(52) U.S. Cl.
CPC .............. *G16H 10/60* (2018.01); *G16H 50/50* (2018.01); *G16B 20/00* (2019.02)

(58) Field of Classification Search
CPC ....................................................... G16H 10/60
USPC .......................................................... 702/19
See application file for complete search history.

(56) References Cited

U.S. PATENT DOCUMENTS

| 2003/0194752 A1 | 10/2003 | Anderson et al. |
| 2005/0137481 A1 | 6/2005 | Sheard et al. |

FOREIGN PATENT DOCUMENTS

| WO | 01/96864 | 12/2001 |
| WO | 03/084388 | 10/2003 |
| WO | 2009/010907 | 1/2009 |
| WO | 2011/133799 | 10/2011 |
| WO | 2012/010871 | 1/2012 |

OTHER PUBLICATIONS

International Search Report and Written Opinion from corresponding International Application No. PCT/GB2014/050240 dated Sep. 17, 2014.
De Beer et al., "Measurement of serum C-reactive protein concentration in myocardial ischaemia and infarction", BR Heart J, vol. 47, 1982, pp. 239-243.

*Primary Examiner* — Jerry Lin
(74) *Attorney, Agent, or Firm* — Tucker Ellis LLP

(57) ABSTRACT

We describe a method of predicting the response of a patient to a medical procedure, the method comprising: inputting acute phase response (APR) biomarker data defining a level of an acute phase response (APR) biomarker in said patient at a succession of biomarker measurement times following said medical procedure, said APR biomarker data defining a biomarker time course representing an evolution over time of said acute phase response; and processing said APR biomarker data to determine a derivative with respect to time of said time course from said APR biomarker data to provide APR time series data; determining a prediction of the response of said patient to said medical procedure from said APR time series data.

12 Claims, 9 Drawing Sheets

SYSTEMS AND METHODS FOR MEDICAL DATA PROCESSING AND ANALYSIS

FIELD OF THE INVENTION

This invention relates to systems, methods and computer program code for processing human (or animal) biomarker data to predict the outcome of a medical procedure, in particular surgery.

BACKGROUND TO THE INVENTION

We have previously described, in WO2012/010871, techniques for predicting the outcome of a medical procedure from the complement cascade response. In addition, WO03/084388 describes a method of detecting early sepsis in a patient which involves monitoring a plurality of biological markers over a period of time; one of the markers mentioned is CRP (C-reactive protein).

Acute phase proteins are proteins whose plasma concentrations increase or decrease in response to inflammation; this is called the acute phase response. Examples of human acute phase proteins are given below:

Human Acute-Phase Proteins

Proteins Whose Plasma Concentrations Increase:
Complement system
  C3
  C4
  C9
  Factor B
  C1 inhibitor protein
  Mannose-binding lectin
Coagulation and Fibrinolytic system
  Fibrinogen
  Plasminogen
  Tissue Plasminogen activator
  Urokinase
  Protein S
  Vitronectin
  Plasminogen-activator inhibitor 1
Antiproteases
  $\alpha_1$-Protease inhibitor
  $\alpha_1$-Antichymotrypsin
  Pancreatic secretory trypsin inhibitor
  Inter-$\alpha$-trypsin inhibitors
Transport proteins
  Ceruloplasmin
  Haptoglobin
  Hemopexin
Participants in inflammatory responses
  Secreted phospholipase $A_2$
  Lipopolysaccharide-binding protein
  Interleukin-1-receptor antagonist
  Granulocyte colony-stimulating factor
Others
  C-reactive protein
  Scrum amyloidal A
  $\alpha_1$-Acid glycoprotein
  Fibronectin
  Ferritin
  Angiotensinogen
Proteins Whose Plasma Concentrations Decrease:
Albumin
Transferrin
Transthyretin
$\alpha_2$-HS glycoprotein
Thyroxine-binding globulin
Insulin-like growth factor 1
Factor XII However acute phase biomarkers are not limited to acute phase proteins and thus also include other acute phase phenomena such as (but not limited to) those below:

Other Acute-Phase Phenomena:
Neuroendocrine changes
  Fever, somnolence, and anorexia
  Increased secretion of corticotropin-releasing hormone, corticotropin, and cortisol
  Increased secretion of arginine vasopressin
  Decreased production of insulin-like growth factor I
  Increased adrenal secretion of catecholamines
Hematopoietic changes
  Anemia of chronic disease
  Leukocytosis
  Thrombocytosis
Metabolic changes
  Loss of muscle and negative nitrogen balance
  Decreased gluconeogenesis
  Osteoporosis
  Increased hepatic lipogenesis
  Increased lipolysis in adipose tissue
  Decreased lipoprotein lipase activity in muscle and adipose tissue
  Cachexia
Hepatic changes
  Increased metallothionein, inducible nitric oxide synthase, heme oxygenase, manganese superoxide dismutase, and tissue inhibitor of metalloproteinase-I
  Decreased phosphoenolpyruvate carboxykinase activity
Changes in non-protein plasma constituents
  Hypozincemia, hypoferremia, and hypcupremia
  Increased plasma retinol and glutathione concentrations These (non-exhaustive) lists of human acute phase proteins and other acute phase phenomena are taken from: Gabay C, Kushner, I. Acute-Phase Proteins and Other Systemic Responses to Inflammation. New England Journal of Medicine 1999; 340(6):448-54.

The conventional biochemical marker for monitoring the acute phase response (APR) during post-operative recovery or infection is C-Reactive Protein (CRP). CRP synthesis is one of a number of proteins differentially regulated by the liver following the local cytokine trigger. The surgical insult initiates the ARP with CRP concentrations rising rapidly, conventionally monitored with an assay having a detection limit of 3 mg/L Changes in the CRP concentration are not detected before 10-12 hrs post-operatively. High sensitivity assays have detection sensitivities of 0.1 mg/L providing information on early-time changes in the patient's recovery but are rarely used clinically.

Current clinical practice is to observe the changes in CRP concentrations, noting the level, rises and falls, but the absolute concentrations of CRP are not useful diagnostically and a poor predictor of complications following abdominal surgery. Some general guidelines exist with concentrations of 150 mg/L on day two post-operatively being indicative of complications but with limited predictive accuracy. Furthermore, investigations on the concentrations of CRP on discharge from ITU appear to have poor prognostic value. Similarly, CRP concentrations measured on the day of sepsis diagnosis appear to be of limited value. The concentration of CRP is a complex function of cytokine stimulation principally interleukin-6 (IL-6), enhanced by interleukin-1β, and the subsequent transcription factors.

The time between the onset of symptoms and subsequent detection and treatment of a complication has been defined as the "time-to-rescue". Shorter time-to-rescue has been demonstrated to result in reductions in ITU length of stay, morbidity, mortality and healthcare costs.

The sensitivity of the APR response and status of the cytokine storm may have important diagnostic predictive value given the large number of potential triggers. The inventor has investigated aspects of the APR response to surgical trauma, secondary complications, and infection which have not been studied previously, with the aim, inter alia, of shortening the 'time-to-rescue'.

SUMMARY OF THE INVENTION

According to the present invention there is therefore provided a method of predicting the response of a patient to a medical procedure, the method comprising: inputting acute phase response (APR) biomarker data defining a level of an acute phase response (APR) biomarker in said patient at a succession of biomarker measurement times following said medical procedure, said APR biomarker data defining a biomarker time course representing an evolution over time of said acute phase response; and processing said APR biomarker data to determine a derivative with respect to time of said time course from said APR biomarker data to provide APR time series data; determining a prediction of the response of said patient to said medical procedure from said APR time series data.

Broadly speaking the inventor has investigated the rate of change of the APR to surgical trauma, complications and infection and has established that this can be used to provide an early warning of either recovery or complications. This can help clinicians to discharge patients when they are ready, freeing up beds earlier, as well as catching the onset of inflammation which could lead to sepsis at an earlier stage facilitating its treatment. As well as being corroborated by clinical data (presented later), anecdotally the information provided by embodiments of the technique appear to correlate with other indications of recovery/complications watched for by clinicians. However embodiments of the techniques we describe can make accurate predictions in some cases more than 24 hours earlier.

Embodiments of the techniques we describe may be used with CRP as a biomarker but other APR biomarkers may also be employed and may, potentially, provide an even earlier response. Such biomarkers include those mentioned in the introduction and include, in particular, SAA (serum amyloid protein A), platelets, and in principle interleukins (although these can be difficult to detect).

Broadly speaking, a maximum in the time derivative data indicates a change of sign of the curvature of the time evolution of the biomarker data, which is indicative of recovery; and vice versa. Ideally the biomarker data would be captured substantially continuously since multiple data points are needed to determine the time derivative (gradient or curvature) but this is not always practical in a clinical setting. Thus a measurement may be taken every few hours, for example every six hours or, rather than round-the-clock regimen, paired tests could be employed, say 6 hours apart, in a morning and afternoon/evening regimen. However in an intensive care setting more frequent measurement could be employed; for example a high resolution CRP assay may be performed in less than 60 minutes, potentially faster with more sophisticated techniques, for example those described in WO2012/010871 (an earlier application of the inventor's).

Some preferred implementations of the technique take account of the clearance rate of the APR biomarker in the patient; a standard value for this may be employed or, in principle, a value for an individual patient may be determined. This can be used to correct the time derivative by adding on a value dependent on the clearance rate to recover a more accurate value for the APR. Embodiments of the technique may also adjust for errors in the clearance rate and/or time derivative data, for example by finding an error and/or disregarding a data value where the derivative has a value defining a rate of fall of the biomarker greater than the clearance rate of the biomarker in the body (which should define the maximum rate of fall of the biomarker).

In some preferred implementations of the method a variable is defined to represent an alert state for the patient, in particular to provide an early warning of a predicted probable complication. This alert state variable may have a value which is updated dependent on one or more detected conditions in the APR time series data. Thus a falling level of the APR response as indicated in the APR time series data after an initial threshold time for example after 10 hours or 20 hours, provides a condition which, if detected, may be used to adjust the value of the alert state variable to increase the probability of a prediction of recovery.

Similarly a fall in the APR time series data when this is updated using a further biomarker measurement can also be used to adjust the alert state variable to increase the recovery prediction probability.

In a corresponding way the value of the alert state variable can be adjusted, for example decreased, to increase the probability of predicting a complication (for example, 'relapse', infection or the like). One example of such a condition is a point of inflection in the APR time series data, broadly speaking a slowing in the fall of the APR response; another is a minimum in the APR time series data; a third is a rise in the APR time series response. In some preferred embodiments these conditions are weighted, more particularly differently weighted so that some conditions have a greater influence on the alert state variable than others. In particular detection of a minimum in the APR time series data may be weighted more than one, or more, or all, of the other conditions as this is a particularly useful early warning of potential complications (albeit not apparent in the raw ARP biomarker data). The particular values of weights for the conditions may be determined, for example, from historical patient data to optimise the predictions of the system. For example a rational determination of weights may be based upon one or more of: curvature of the APR; the second derivative of the CRP time course; and other analytic time course analyses of the data including, but not limited to: curvature, Fourier Transform, area-under-the curve, time to maximum, maximum rate of production of CRP, maximum possible drop in CRP against a known or preset value. Some, any or all of these may then be used to weight the response. For example if a weight is too small the predictive response may be too sluggish whereas if it is too large it may be over sensitive to noise in the data.

Optionally in embodiments the alert state (more particularly the value of the alert state variable) may be employed to trigger (suggest) an intervention, which may then produce a care pathway (or a selection from amongst a set of care pathways) controlled by the APR alert (state variable).

In some preferred embodiments of the technique a prediction of a probability of a complication is determined by a Bayesian technique, determining a conditional probability of the complication dependent on the alert state variable. More particularly the probability of a patient response (which may include one or more of: recovery and one or more different types of complication), given the value of the alert state variable, may be determined from a product of a likelihood of the value of the alert state variable given the response and the prior probability of the alert state variable (optionally normalised by the marginal likelihood of the response).

Thus, for example, the probability of an anastomotic leak given a particular value for the alert state variable, say 3, may be determined from the probability of that value for the variable given an anastomotic leak multiplied by the prior probability of that value for the alert state variable and, optionally, divided by the marginal likelihood of the anastomotic leak.

Helpfully these terms in the Bayesian model may be determined retrospectively from historical patient data knowing, for example, values of, say, CRP levels and patient outcomes (leak or no leak—typically known from surgery). This data may be obtained for a range of different complication types and the techniques we describe can then be used to provide a prediction of a complication some 24-36 hours in advance of what would hither to have been taken from the biomarker levels.

The skilled person will recognise that although we have described a technique which, in embodiments, works with one ARP biomarker, the technique may be extended to determine time series derivative data for a plurality of different ARP biomarker levels. Conditions in the APR time series data as previously described may then be determined for each of these and this information may be used either to update a common alert state variable or to update separate alert state variables for the biomarkers. In the latter case the probabilities determined from the different alert state variables may be combined, for example using a Bayesian approach as described above. In addition it can be desirable to 'triangulate' the prediction by further clinical investigation, for example a CT (computer tomography) scan to confirm a predicted leak or otherwise. Additionally or alternatively a prediction may be combined with or made from a nomogram, that is a graphical or other representation may be defined for a normal or expected APR response, and then a deviation from this path determined (either graphically or otherwise) to predict or determine the probability of one or more complications.

The above described approaches may be extended so that a probability of a complication is dependent on a co-morbidity of the patient, that is upon one or more other pre-existing conditions of a patient. This may be achieved, for example, by segregating the values in the aforementioned Bayesian probability calculation by disease or disorder, determining separate likelihood functions for the separate cohorts of patients. Again this may be done retrospectively based on historical collected data. This can provide a significant improvement in the prediction of complications for, for example patients with diabetes, cystic fibrosis, heart disease or any of many other co-morbid conditions by which the data may be segregated.

In embodiments the ARP biomarker comprises CRP, and the determining of the prediction comprises evaluating:

$$ARP(t) = \frac{dCRP(t)}{dt} + k_C$$

where $k_C$ is the clearance rate of CRP, principally, by the liver. The skilled person will appreciate that whichever biomarker is employed, the Bayesian probability, and also prior and likelihood functions, are functions of time.

In one implementation embodiments of the technique may simply identify recovery of the patient, to facilitate early discharge, or relapse of the patient after an initial period of recovery. However in principle a set of complications which may comprise substantially all the usual complications, may be defined and the probability of each determined, by the aforementioned techniques.

In a related aspect the invention provides a computer program for predicting the response of a patient to a medical procedure, wherein the program is configured to: input APR biomarker measurement data defining a level of an APR biomarker; update APR biomarker time series data for said APR biomarker responsive to said APR biomarker measurement data; determine a time derivative of said updated APR biomarker time series data to determine updated APR data; update stored time series of said APR data with said updated APR data; identify one or more time dependent conditions in said stored time series of said APR data; update a value of an alert state variable responsive to said identification of said one or more time dependent conditions; and predict said response of said patient dependent on said value of said alert state variable.

Again time-dependent conditions may be identified as previously described and used to predict the response, which may comprise recovery and/or one or more identified complications. Again one preferred implementation employs a time derivative of CRP calculated in combination with a clearance rate, as described above.

The method may also include performing an assay to determine a level of each APR biomarker. This may be determined, for example, from a blood sample from the patient.

The invention further provides processor control code (computer program code) to implement the above-described systems and methods, for example on a general purpose computer system or on a digital signal processor (DSP). The code is provided on a carrier such as a disk, CD- or DVD-ROM, programmed memory such as non-volatile memory (e.g. Flash) or read-only memory (Firmware). Code (and/or data) to implement embodiments of the invention may comprise source, object or executable code in a conventional programming language (interpreted or compiled) such as C, or assembly code. As the skilled person will appreciate such code and/or data may be distributed between a plurality of coupled components in communication with one another.

In a related aspect the invention provides a medical procedure outcome prediction system, the system comprising: working memory; program memory; a processor coupled to said working memory and to said program memory; an input to receive APR biomarker data comprising data representing a level of an acute phase response (APR) biomarker in said patient at a succession of biomarker measurement times following said medical procedure, said APR biomarker data defining a biomarker time course representing an evolution over time of said acute phase response; and wherein said program memory stores processor control code to: process said APR biomarker data to determine a derivative with respect to time of said time course from said APR biomarker data to provide APR time series data; and determine a prediction of the response of said patient to said medical procedure from said APR time series data.

The invention still further provides a computer system program for the computer program as described above.

BRIEF DESCRIPTION OF THE DRAWINGS

These and other aspects of the invention will now be further described, by way of example only, with reference to the accompanying figures in which.

DETAILED DESCRIPTION OF PREFERRED EMBODIMENTS

Figure 1:
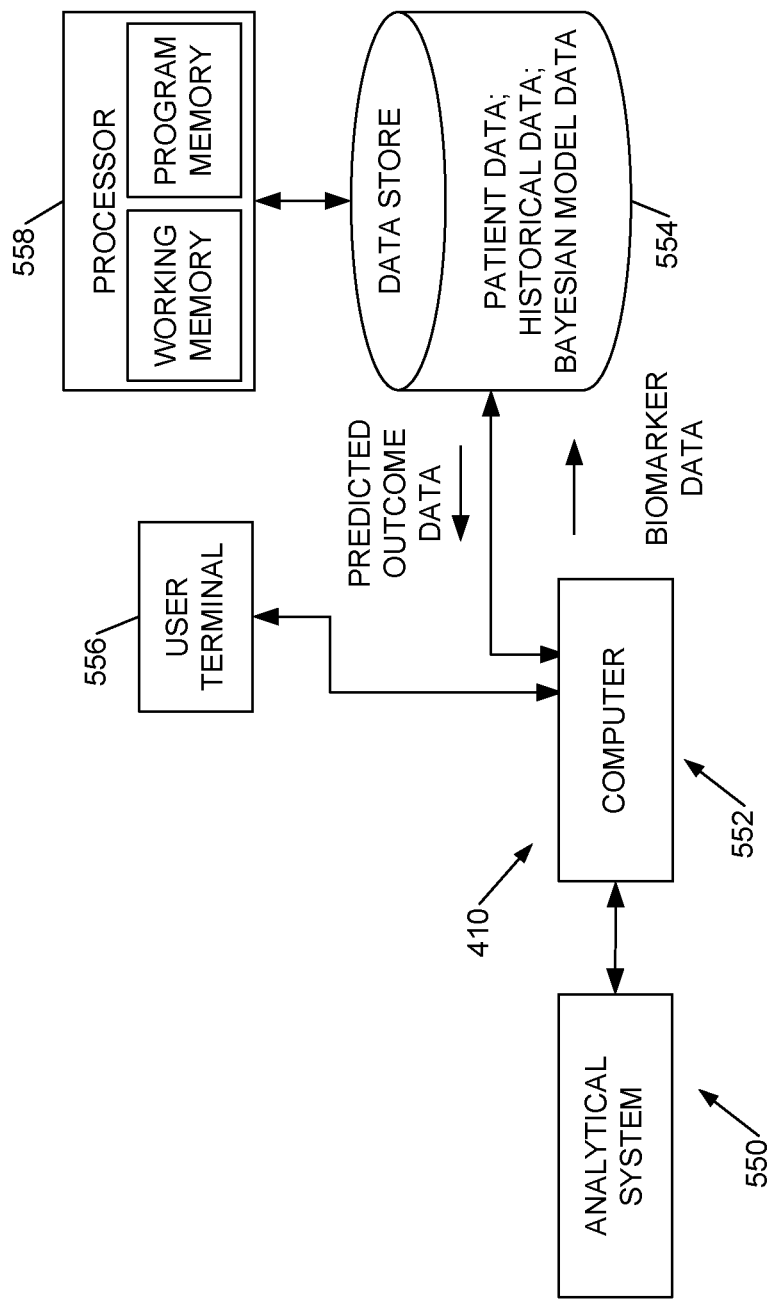
FIG. 1 shows data processing apparatus configured to implement embodiments of methods according to the invention.

Referring to FIG. 1, this shows an analytical system 550 is coupled to a computer system 552 which performs signal processing on the data from the apparatus to determine biomarker level data representing levels of a plurality of APR biomarker levels. The system also interacts with a database 554 which includes a data to implement a model as described above to predict patient outcome, and provides a user terminal 556 for interacting with the system and outputting the prediction data. In embodiments the database is coupled to a further computer system 558 comprising working memory and program memory, the program memory storing code to use the model data to predict the outcome of a medical procedure on a patient as described.

In embodiments the data store 554 stores patient data, more particularly a time series of patient APR biomarker data, and APR time derivative data, calculated by the computer, as well as optionally historical data for contrasting the Bayesian model, and the model data itself, representing a statistical model for determining one or more patient outcomes from the APR biomarker data.

The rate of change of the APR to surgical trauma, secondary complications or infection has not been studied previously. The APR time profile and the switch of the protein synthesis in hepatocytes lead to a rise in the serum CRP concentration. In contrast, processes leading to a fall in the CRP concentration include the proposed role of CRP in Classical Pathway Complement activation and the clearance process. Clearance is dominated by liver breakdown leading to a half-life determination of 19 hours, which has been proposed to be constant under all conditions of recovery and disease, although this may need qualification. The time course profile of CRP represents the cumulative effect of all of the competing production and removal processes following the initial surgical trauma, which are then re-stimulated with the subsequent onset of complications.

A differential analysis of the CRP time course profile may provide information on the APR and a systems-level diagnostic of recovery or the onset of complications. The systemic response is personal to the patient's recovery pathway and co-morbidities dictating the patient's degree of defensive response and recovery. Whilst the level or response may not be indicative the changes associated with the different triggers and the duration of the response may be critical to the patient outcome. Dynamic visualisation of the APR may provide a personalised marker of recovery and rapidly reduce the time-to-rescue for all complications. The aim of our study is to profile the time course of CRP and derive the dynamics of the APR in response to surgical trauma.

Methods

Patients and Setting

Figure 2:
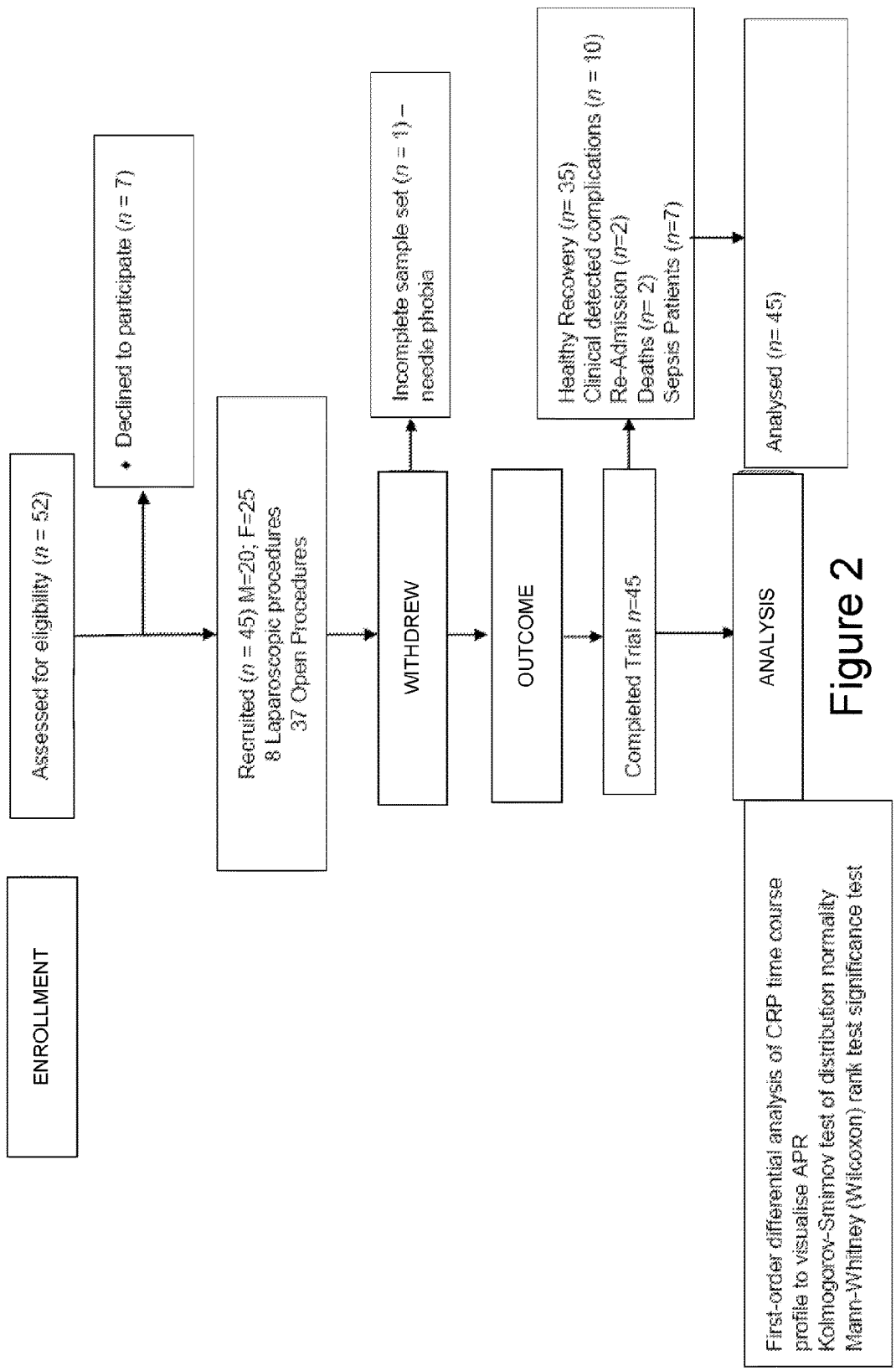
FIG. 2 shows the Consort plot for the design of the pilot trial.

Consecutive patients undergoing elective colorectal or urological surgery at The Royal Devon & Exeter Hospital were considered eligible for recruitment. The study recruited a cohort of 45 patients detailed in the Consort plot, FIG. 2. Blood samples from participants were collected over the time course: t (hours)=admission, 0 (induction of anaesthesia), 1, 2-4, 8, 12, 24, 36, 48 (from induction) and as requested by the clinicians routinely until discharge from hospital. The CRP measurement was performed with the standard assay available in the Clinical Chemistry laboratory. Patient exclusion criteria were deliberately low to recruit a full spectrum of procedures, however, the following exclusions were imposed: unable/unwilling to provide informed consent, pregnant women, patients less than 18 years of age, diabetes, inflammatory bowel disorders, immune-suppressed, immune-suppression or steroid treatment within the last 12 months. The patient data, assay results and clinical observations were anonymised by the clinicians and recorded with encryption and password protection.

Mathematical Analysis of the CRP Time Course

The time course CRP data were interpolated using a Piecewise Cubic Hermite Interpolating Polynomial (PCHIP) preserving the shape and first derivative of the serial time course. The interpolated data were re-sampled to replace any missing time course data points. Numerical first and second derivatives were calculated using the trapezium rule. Mathematically, the rates of CRP production and consumption were represented by the derivative of the concentration with respect to time, given by the following first order differential equation:

$$\frac{d[CRP]}{dt} = APR(t) - k_C[CRP] \qquad \text{Equation 1}$$

where d[CRP]/dt is the first derivative, APR(t) is the acute phase response over time and $k_C$[CRP] is the rate of clearance from the liver, [CRP] is the concentration and $k_C$ is the first-order clearance rate constant defined by the half-life. (10) The APR was determined by re-arranging Equation 1:

$$APR(t) = \frac{d[CRP]}{dt} + k_C[CRP] \qquad \text{Equation 2}$$

The concentration of CRP is measured as a function of time and so the APR can be derived. Subsequent re-sampling of the data for 6-hour intervals and calculation of the APR were based on the same equations.

Statistical Analysis

The statistical analysis was performed using the MatLab implementation of the algorithms. The concentration distributions at each time point were tested for normality using the Kolmogorov-Smirnov test, $H_0$ null hypothesis being a normal distribution, $H_1$ non-normal distribution. The entire data set is plotted as a combined bee-swarm boxplot where required. Non-parametric mean and 95% confidence limit were performed by bootstrap re-sampling based on 1000 re-samples of the 45-sample data set. Statistical analysis of the significance in difference in the median of populations was performed using the Mann-Whitney (Wilcoxen) rank test.

Definitions

A clinical complication is defined as any deviation from the normal post-operative course detected and recorded by clinical team and is graded using the Clavien-Dindo classification. A secondary maximum in the CRP concentration was used as a dichotomous biochemical marker of further APR to a presumed complication.

Results

A cohort of 45 patients were recruited from 52 patients approached for consent giving a recruitment rate of 85% (25 males and 20 females. The median operative time was 154 minutes (range 105-205) with the median length of stay of 200 hours (range 94-199 hours). Eight procedures were laparoscopic and the remaining 37 procedures were performed by open surgery.

Figure 3:
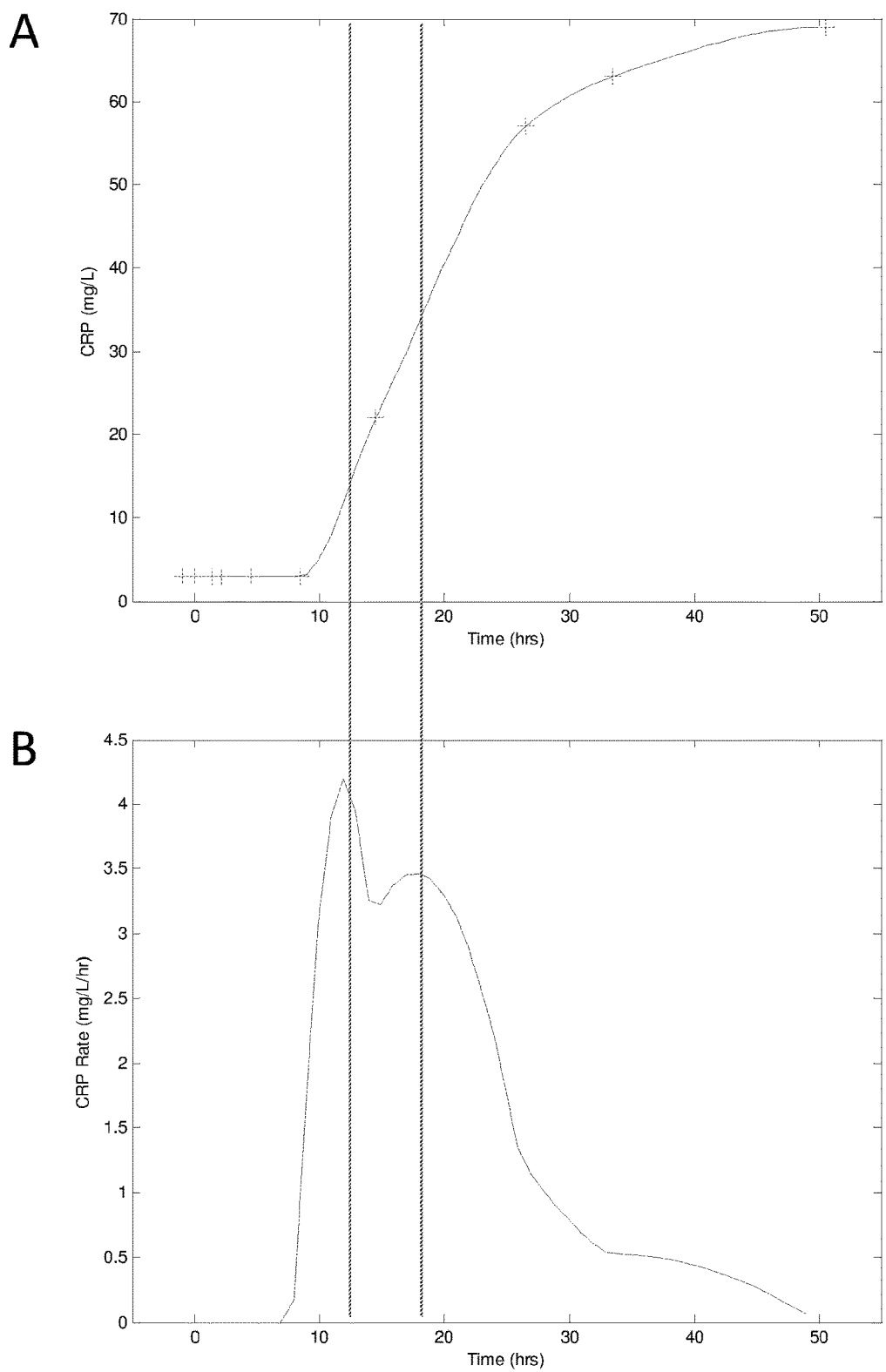
FIG. 3 shows a CRP time course over a 50 hour period from a patient recovering from major abdominal surgery. A: The time course data points are interpolated using a method that preserves the continuity and slope of the time course such as Piecewise Cubic Hermite Polynomials; B: the interpolated trace may then be differentiated numerically to produce the numerical derivative. The vertical lines indicate points of inflection

A CRP time course for a typical uncomplicated recovery following surgery is shown in FIG. 3. The CRP rises initially at 8 hours when the concentration is greater than 3 mg/L, FIG. 3A. The CRP continues to rise throughout the 48-hour period of the trial, reaching a maximum of 68 mg/L. The rate of CRP production, equal to the first derivative, rises to an early maximum at 12 hrs of 4.2 mg/L/h, FIG. 3B, midway along the rise in the CRP concentration and 18 hrs before the CRP concentration reaches its maximum. The maximum in the rate of CRP production defines a point of inflection on the CRP concentration time course profile. Similar points of inflection would be present on a falling CRP concentration or a secondary rise following a further stimulation of an APR due to a complication such as anastomotic leak, infection or internal bleeding.

Figure 4:
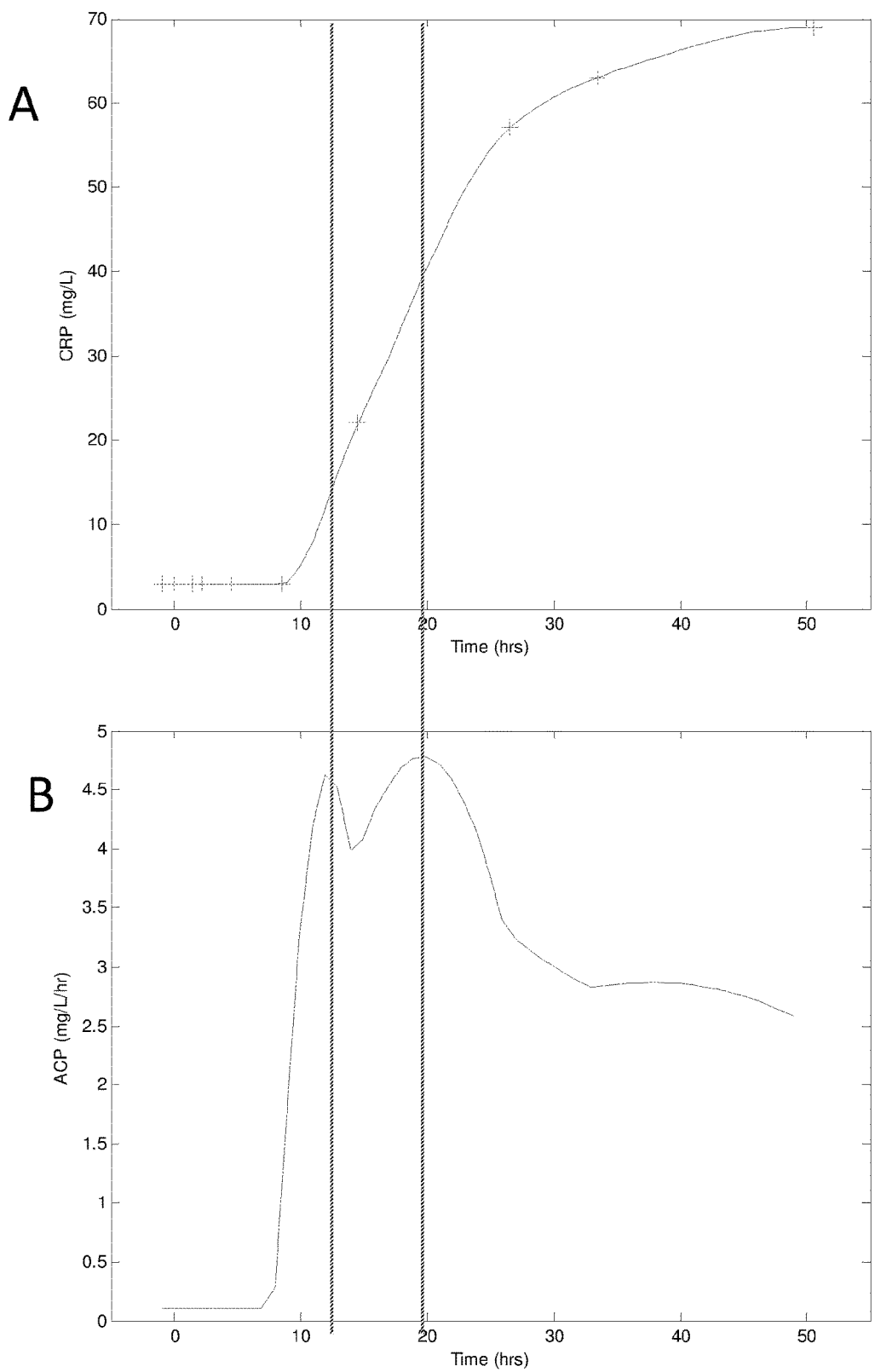
FIG. 4 shows the APR derived from the numerical derivative of the CRP time course with the addition of the term quantifying the CRP clearance rate: A is the CRP time course reproduced from FIG. 3 and B is the APR derived from equation 2. The APR maximum is shifted to longer time than the point of inflection.

The APR may be visualised using the clearance term in Equation 2 and the numerical derivative, FIG. 4. The CRP time course is reproduced in FIG. 4A and the corresponding APR show in FIG. 4B. The position of the APR maximum shifts slightly longer in time following the clearance rate correction but only be a few hours.

Figure 5:
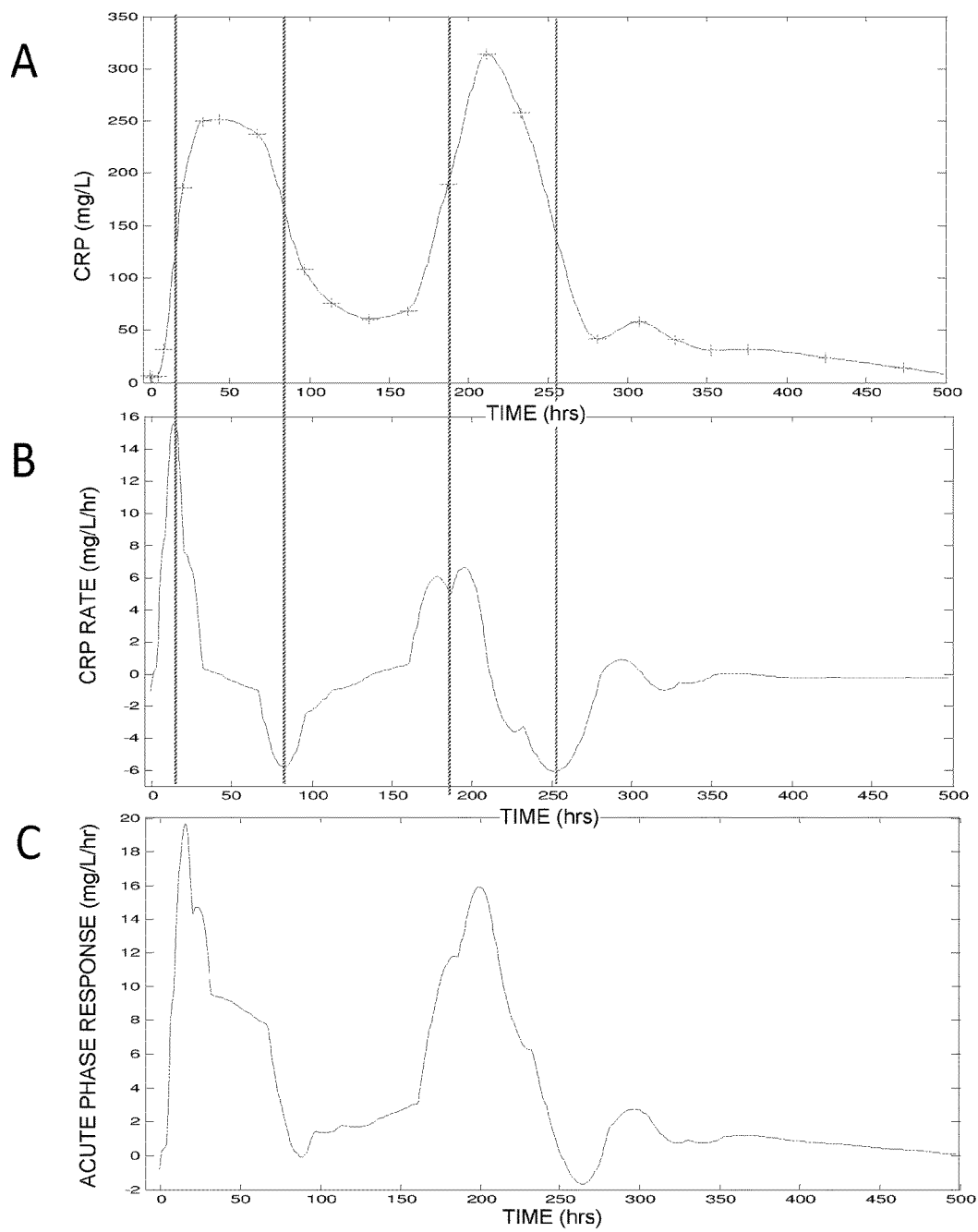
FIG. 5 shows A the CRP time course profile; B the numerical derivative; and C the APR visualisation for a patient with a post operative complication (ileus).

A CPR time course for a complicated recovery is shown in FIG. 5A; FIG. 5B shows the numerical derivative of the CRP time course, and FIG. 5C the derived APR response: the CRP concentration again passes through a point of inflection after 18 hours in following surgery, reaching the first maximum at 50 hrs. Then as the CRP concentration begins to fall there is a second point of inflection 70 hrs (negative going in FIG. 5B) ahead of the minimum in CRP at 140 hrs and the first increase in CRP concentration at 170 hours. A third point of inflection occurs in the CRP time course 190 hours ahead of the second maximum at 212 hrs. A fourth point of inflection occurs at 260 hrs before a third APR response at 320 hrs. The patient developed clinical symptoms of ileus at 72 hrs (Clavien-Dindo (CD) I). Similar CD classifications of complications were assigned to all complications recorded in the clinical notes for 10 out of 13 complications. CD classifications evolved with the time course and varied of the full range from I-V, however three double-maximum complications were observed and not recorded clinically. The differential analysis of the time course revealed changes in the APR that were not recorded clinically either as a result of a non-clinically presented complication or a miss-interpretation of a rising CRP as a large single maximum.

Figure 6:
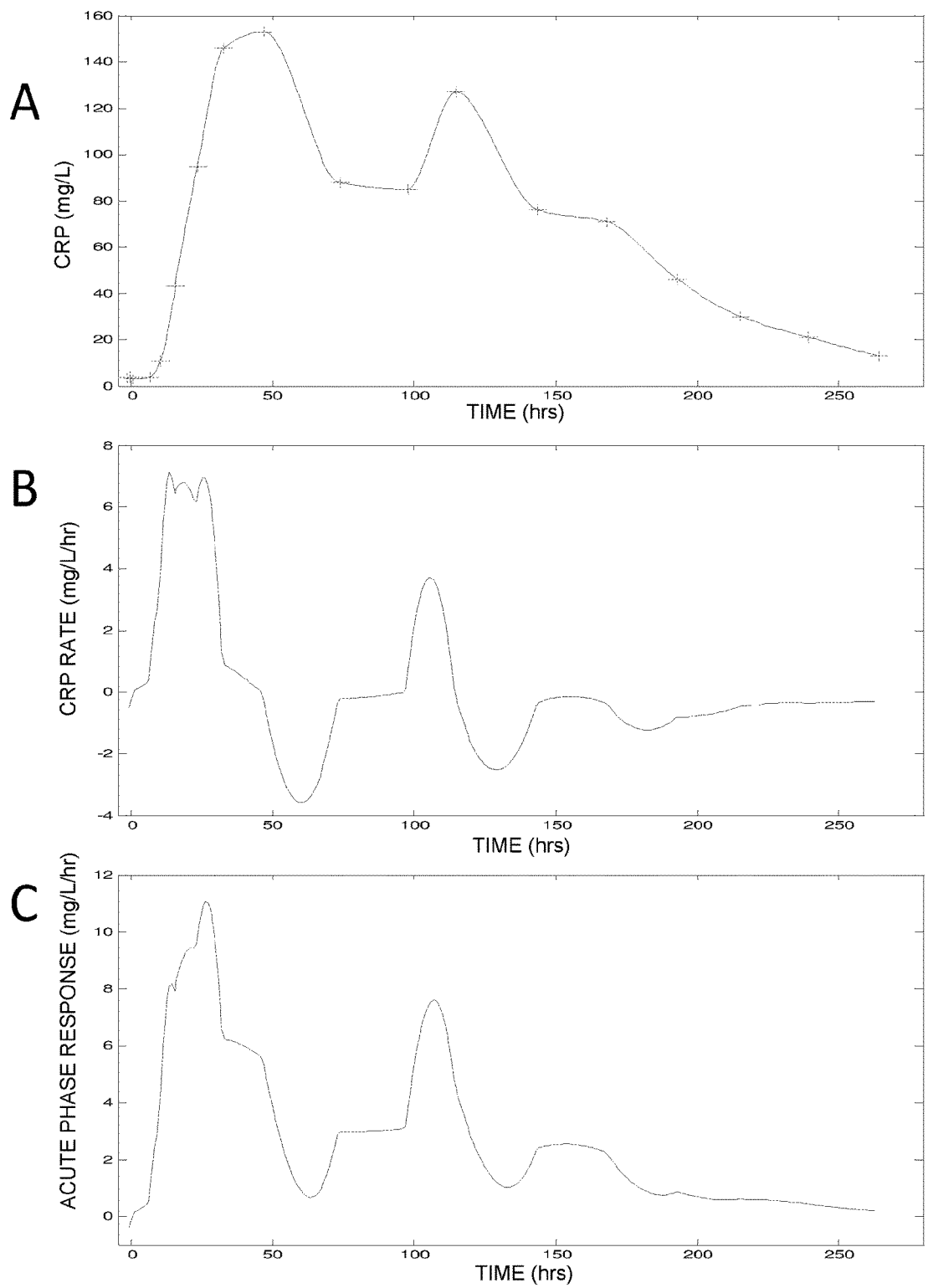
FIG. 6 shows the A CRP time course, B the first derivative and C the derived APR response for a recovery showing complications and may be compared with FIG. 5. Complications occur at different times unique to the recovery of the patient.

The APR for the complicated recovery may be derived using the clearance rate proposed in the literature in Equation 2. The APR for this patient's recovery is shown in FIG. 4B. The positions of the maxima in the APR are shifted slightly to earlier time by the clearance term. A second complicated recovery is shown in FIG. 6 with the CRP trace, FIG. 6A, the numerical derivative FIG. 6B and the derived APR FIG. 6C. Complications for all patients depend significantly on the nature of the complication and the patient's response and the times of points of inflection or other turning points are intimately related to the individual patient's recovery.

The initial APR to the surgical insult results in a maximum in CRP concentration within 48-72 hours of induction of anaesthesia, which must always be preceded by a point of inflection with a 100% positive predictive value (PPV). The time to the point of inflection in the CRP time course is compared with the time to maximum, FIG. 3-6. The time-to-inflection is not normally distributed in the cohort (Kolmogorov-Smirnov test, $H_1$ is true with $P<10^{-9}$) and similarly for the time-to-maximum ($H_1$ is true with $P<10^{-9}$). The median value for the time-to-inflection is 17 hours (16-18 hours, 95% bootstrap confidence limit); the time-to-maximum distribution has a median of 44 hours (42-47 hours, 95% bootstrap confidence limit). The medians are significantly different at the 95% confidence level using the Mann-Whitney (Wilcoxon) test, rejecting the hypothesis of equal medians with $P<10^{-9}$.

Figure 7:
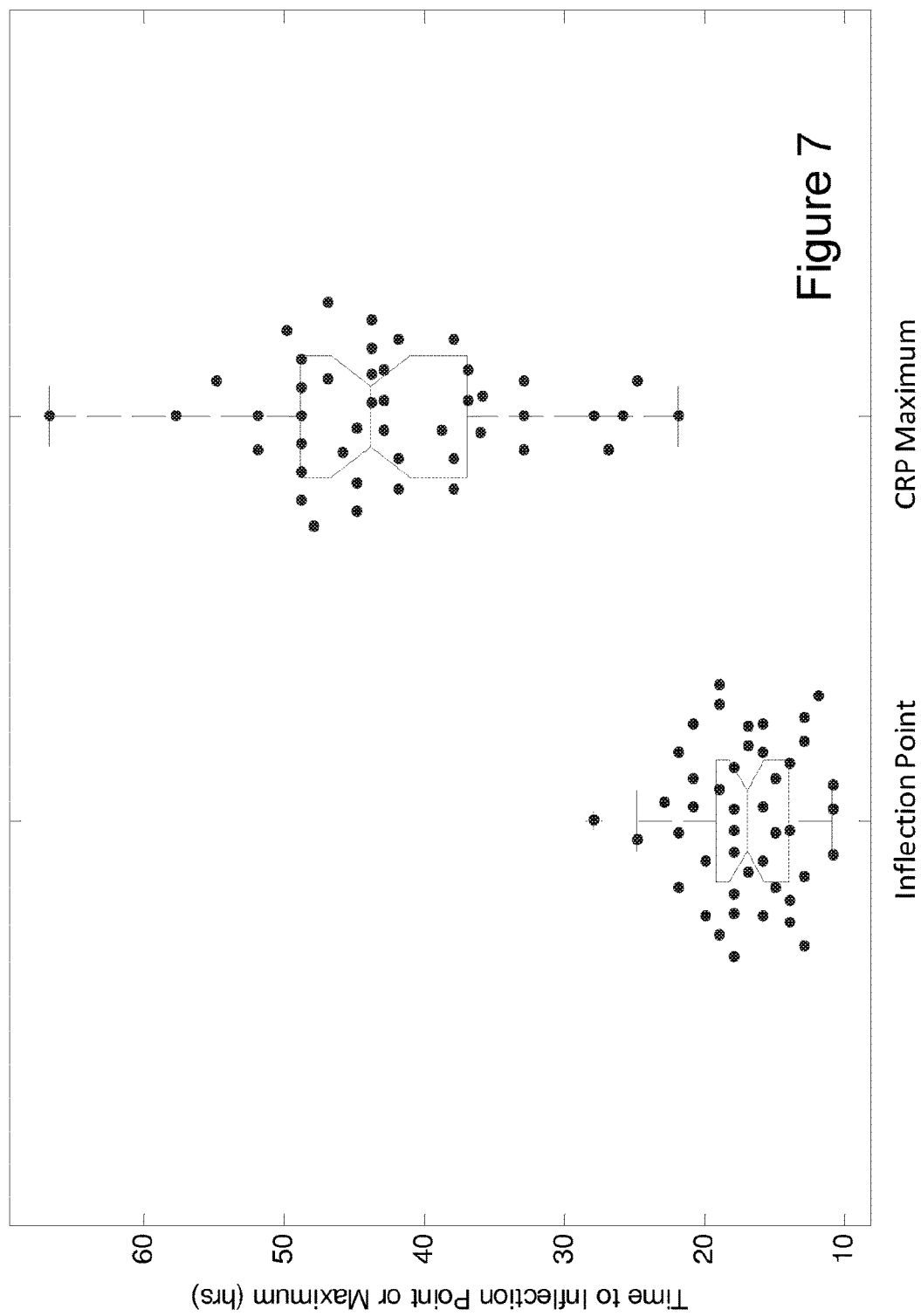
FIG. 7 shows the box and whisker plot for the median time to point of inflection and median time to CRP maximum. The point of inflection is significantly shorter (95% confidence, $P<10^{-9}$) 27 hours before the CRP maximum. The box notches represent the 95% confidence limits.

FIG. 7 shows a box and whisker and bee swarm plot for the median time to inflection and time to CRP maximum. The Boxes contain notches at 95% of confidence limits; notches not overlapping indicate significant different in the medians; $P<10^{-9}$.

Figure 8:
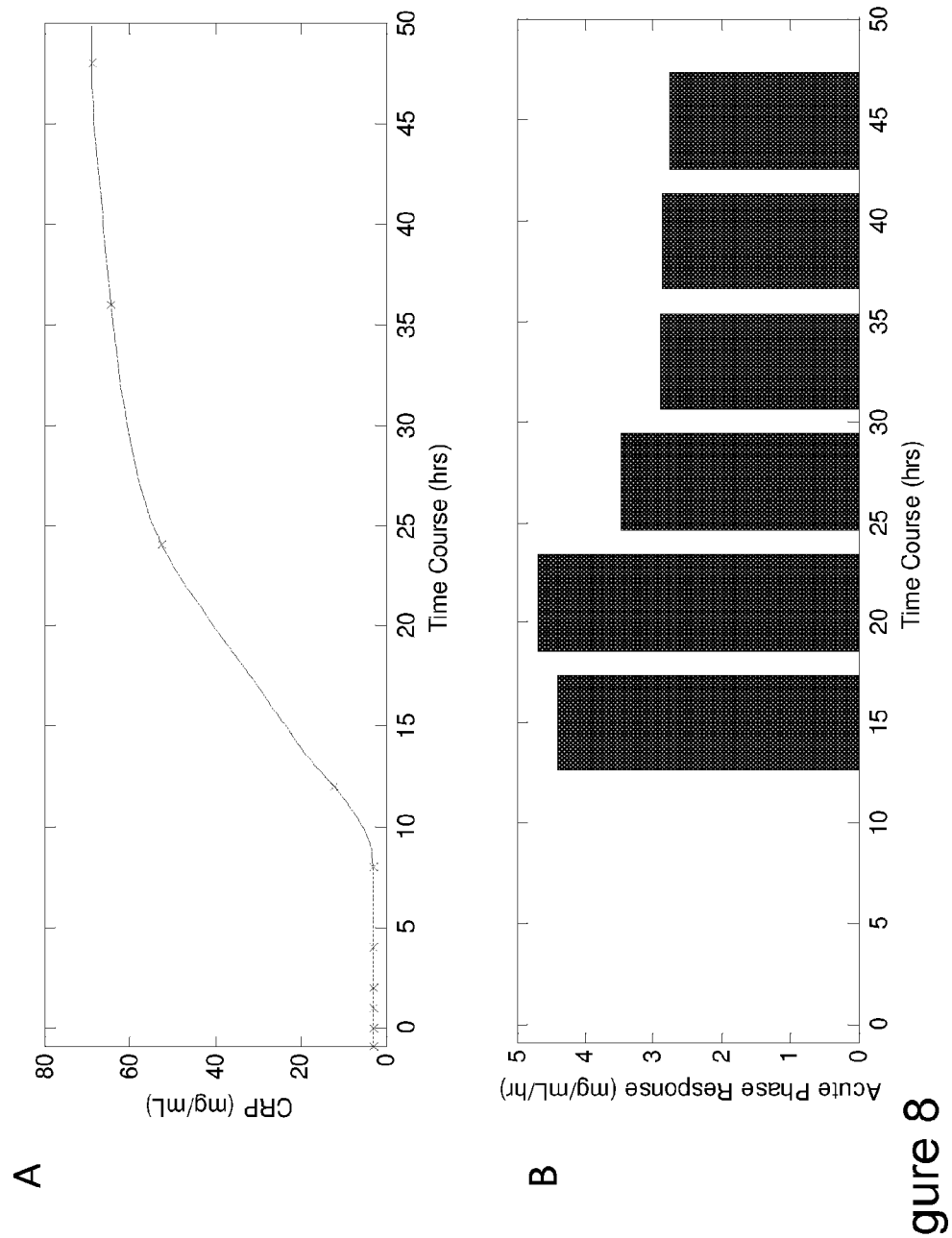
FIG. 8 shows A CRP time course; and B the derived APR response re-sampled at 6-hour paired time points for a patient showing uncomplicated recovery in FIG. 3. The point of inflection is captured by the 6-hr paired samples and the APR decreases throughout the recovery.
Figure 9:
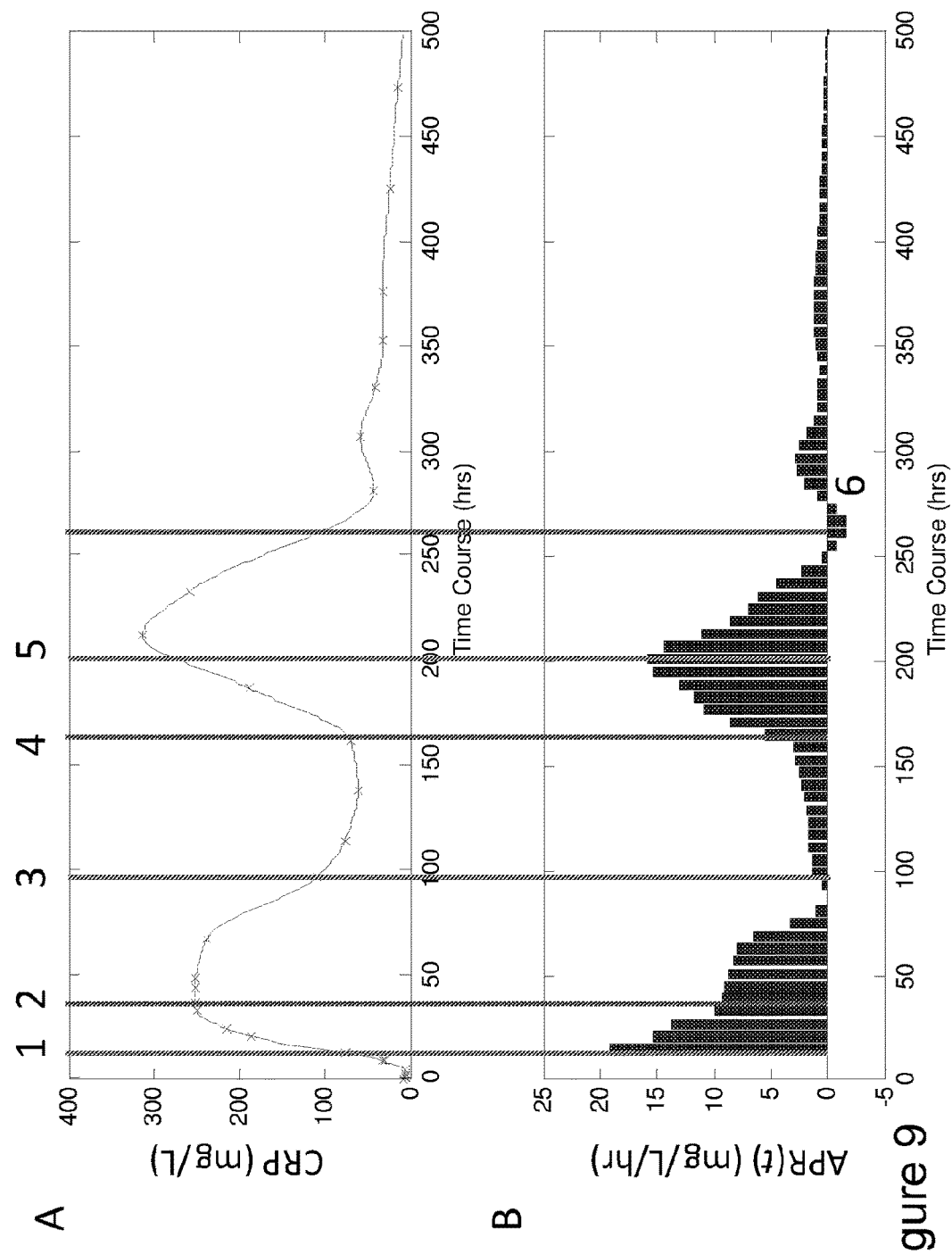
FIG. 9 shows a 6-hour simulated time profile for a complicated recovery showing A CRP and B the acute phase response (APR). The APR visualisation shows changes for all CRP changes earlier than the clinically relevant response in the CRP (a change in magnitude). The APR produces an clinically intuitive marker of the recovery.

Re-sampling the CRP time course data at a 6-hour interval indicates changes that should be detectable at the accuracy of the CRP assay in the laboratory, FIG. 8 and FIG. 9.

Discussion

The time course profile of CRP post-operatively is triggered by the APR to the surgical trauma. The local release and synthesis of cytokines predominantly IL-6, cause a change in the protein production pattern of the liver, differentially regulating a number of proteins including CRP, Serum Amyloid A and Complement. The de novo synthesis of CRP starts promptly following the regulatory changes but is not detected at present until it is greater than the assay maximum at 3 mg/L and clinically above the normal reference ranges, 0.07-8.2 mg/L.

The shape of the CRP time course profile is then a balance of the processes leading to the production of CRP, principally derived from the APR and those processes that cause the decrease of the CRP concentration, dominated by clearance through the liver. The balance suggests that a differential analysis of the CRP profile, initially the gradient contains information about the APR and the clearance rate.

When the rate of CRP production equals the rate of clearance, the CRP concentration reaches a maximum, FIG. 3A and this corresponds to zero in the gradient, FIG. 3B. CRP has a half-life of 19 hours reportedly under all disease states, although this assumption may be worth revisiting especially during organ failure. The patient-to-patient variability in the clearance rate is unknown and is likely to depend significantly on patient co-morbidity. The APR and first derivative of the CRP trace are numerically related by Equation 2 whatever the assumptions about the clearance process or other terms not explicitly present in the equation. CRP may be removed from the circulating blood by consumption processes such as binding to damaged or foreign surfaces within the body. The proposed role of CRP as a primitive antibody capable to triggering the Classical Complement pathway would result in CRP being removed from the circulating blood observed as a decrease in the concentration and an apparently higher clearance rate than the proposed 19-hr half-life would suggest.

Based on the 19-hr half-life assumption, the CRP concentration in FIG. 3A would take 3 days to return to normal levels from clearance alone.

Irrespective of the clearance, the rate of production of CRP must initially rise and then pass through the point of inflection associated with the maximum in the APR. The point of inflection is mathematically required on a continuous curve and has a PPV of 100% for all maxima or minima. The point of inflection in the CRP slope must occur before the CRP concentration maximum, FIG. 6 for the APR associated with the surgical trauma. Similar points of inflection in the CRP slope must occur before all minima or maxima with the same PPV, although the time period at which it occurs before the minimum or maximum depends the nature of the underlying APR. In our cohort, time to inflection and time to maximum showed only small patient APR variability.

The slope of the CRP time course is therefore an early and sensitive marker of the APR with the point of inflection providing a well-defined biochemical marker of the onset of recovery. Measuring the CRP concentrations more frequently would capture the initial point of inflection and any subsequent inflections more accurately. A series of paired CRP tests, 6 hours apart starting at 12 hours post-induction, would allow the maximum in APR to be determined and mark the biochemical onset of recovery. The 6-hr paired test is calculated for the normal recovery and is shown in FIG. 8. There is an early rise in the APR followed by the fall capturing the point of inflection and marking the biochemical onset of recovery within the first 24 hours, consistent with the clinical observation that patients show signs of recovery within the first post-operative day. A 6-hour simulated time profile for the complicated recovery is shown in FIG. 9. This demonstrates the onset of complications is present in the APR profile much earlier than the CRP concentration change, potentially producing an alert 71 hours and subsequent reduction in time-to-rescue.

There are two significant limitations to the methodology. Firstly the assumption of a constant CRP clearance half-life of 19 hours is illustrated by the apparent negative APR response in FIG. 9 at point 6. This indicates that the CRP half-life for this patient is over estimated using the literature value. This overestimation occurs in only 10% of cases in the cohort; the degree of underestimation is unknown. The constant half-life assumption is however not limiting to the analysis and the generation of APR alerts. The precise dynamics of the APR will depend on the personalised response to different stimuli, expecting differences to anastomotic leak or paralytic ileus and different in each patient. Secondly, the current time course analysis relies on the PCHIP interpolation, which unlike spline fits, preserves the slope of the underlying data. The derivative of the interpolated fit shows some imperfections giving rise to the apparent double maxima in the derivative shown in FIGS. 3-6. These are processing artefacts that would not be present in the 6-hour paired profiles, such as in FIG. 7 and FIG. 8.

Acute Phase Response Alerts

The 6-hr paired APR profiled provides the clinician with an easily interpreted visual representation of the recovery, rising and falling rapidly in a clinically useful timescale. The APR can be used to produce a series of APR Alerts which would allow the clinical chemistry laboratory or the ward nurses to trigger a clinical re-appraisal. An early warning system (EWS) is currently used on the ward derived from the clinical observations. As series of alerts based on the CRP time course can be constructed that is dependent on the type of procedure, type of complication and stratified for patient co-morbidities. A retrospective and prospective analysis by surgical procedure will inform the predictions.

The alert system for each procedure type and stratification may be tested for positive and negative predictive values (PPV and NPV) reported at the time of the alert against the EWS and clinical judgement. The distributional information based on the retrospective and prospective analyses can be used to inform on the prevalence of a complication at particular times to create a Bayesian prediction:

$$P(\text{Complication Type} \mid APR\ AlertState) = \frac{P(APR\ \text{Alert State} \mid \text{Complication Type}) P(APR\ \text{Alert State})}{P(\text{Complication Type})}$$

Where the probabilities of complication type given an APR Alert state, P(Complication Type|APR Alert State) is informed by the historical distributions of complications types in time. The probability will also evolve in time. The Bayesian probability hypothesis test can be given an accurate confidence.

The possible outcomes from a surgical procedure form set of results that may be written for example (but not exhaustively) as:

C0—uncomplicated recovery
C1—Anastomotic Leak
C2—Ileus
C3—Secondary Infection
C4 Pneumonia
C5—SIRS
C6—Sepsis Each of which would be characterised by APR response characteristic pattern, APR temporal profile and a prior distribution derived from retrospective and prospective data. With a sufficiently large data set, this could be resolved by co-morbidity, age and procedure type. At each time point in the recover an APR Alert state can be calculated to provide the clinician with a trigger to re-assess the patient and a possible likelihood of complication given the prior knowledge of the APR profile.

The choice of APR Alert criteria and the relative weightings assigned to the changes in the APR is shown in Table 1. The current APR is assessed for changes in the CRP gradient and the changes in the APR response to produce a series of scores: eg rising APR causes a rise in the Alert State from APR Alert 1-APR Alert 3. The presence of a point of inflection in the APR (the second derivative of the CRP time course) predicts a minimum and would cause a larger jump in the APR Alert state. A series of thresholds can be set such as APR Alert 4 would trigger a clinical re-evaluation with the C0-6 probability distribution calculated at each stage. The weightings and precise formulation of the APR Alert state triggers such as those presented in Table 1 would be refined by procedure with retrospective and prospective data to minimise the false positive and false negative alert states using the full analysis of diagnostic accuracy such as ROC curves.

TABLE 1

Alert State Criteria

| Alert State Scale | Alert Criteria | Alert State | Bayesian Predictions |
|---|---|---|---|
| Falling APR after 20 hrs expected recovery profile | Green | Green 0-2 | C0 |
| Continuing fall throughout stay | Green | | C0 |
| Slowing the in APR fall | +1 | Amber - 2-4 | Complications Profile C1 = 25% C2 = 45% C3 = 10% C4 = 10% C5 = 5% C6 = 5% |
| APR minimum | +2 | Red 3 and above | Complications Profile C1 = 5% C2 = 25% C3 = 10% C4 = 10% C5 = 25% C6 = 25% |
| Rising APR at each test | +1 | | Etc . . . |
| Falling APR | −1 | | |

The Alert State Criteria can be derived for procedure, co-morbidities and illnesses and will include the complications profile and prevalence for each procedure from the prospective and retrospective data. A full interventional trial based on the Alert State will produce a Care Pathway Management Strategy.

Target Procedures include: sepsis, pneumonia, colorectal surgery, urological surgery, general abdominal surgery, acute appendicitis, orthopaedic surgery, peritonitis etc.

The APR Alerts will be optimised for each procedure and tested against Bayesian Predictions, positive and negative predictive values.

APR Nomograms can be constructed to show and average recovery for a large group showing the predicted APR recovery curve without complications. Deviations from the nomograms can then be used to assess the recovery pathway provide addition indicators of recovery or onset of complications.

The APR Alert can be triangulated with other data, for example but not exclusively, Imaging data so a positive confirmation of an anastomotic leak will set an anastomatic leak recovery pathway from which new deviations can be assessed.

Visualising the APR using the differential analysis of the CRP profile could provide a personalised response to all inflammatory processes with a sensitivity and specificity. Some APR responses indicating complications may not present clinically and a real-time analysis and alert may ensure all complications are noted. Changes in the APR are likely to be more sensitive to changing APR states than the absolute CRP concentrations. The APR changes can be used to generate a series of APAs that are intrinsically personalised depending on the trauma or infection level for each patient and their response to it. The stratification of patients based on time-to-respond and length-of-response can be investigated against exist pre-clinical classifications, co-morbidities, and severity of complications. The analysis is not limited to post-operative recovery but may be applied to all recoveries from infections such as pneumonia and may be useful in assessing the efficacy of drugs or interventions. The onset of recovery marked by the waning of the APR could be used to manage antibiotic treatment regimens, limiting community exposure to antibiotics. APAs could become companion diagnostics to all therapies allowing, for example, an early switch from antibiotics to anti-fungal drugs in acute care scenarios. Further, a fit-to-discharge criterion based on APAs could trigger a clinical assessment and prompt discharge to deliver bed management improvements. The health economic impact and benefits to patient outcome would then be realised promptly. Importantly, these early intervention advantages may be achieved using the existing CRP assays.

Thus, broadly speaking we have described a method/system in which the Acute Phase Response (APR) may be visualised from the first derivative of any acute phase marker or event. The ARP is a marker patient health and indicative of good recovery or secondary inflammatory events. The time course variation of CRP is an example of an acute phase protein from which the APR may be derived. Different acute phase proteins or events characterise the APR and can be "triangulated" (predictions may be confirmed by other clinical investigation). Different acute phase proteins can be used to produce APR sub-system responses using the associations indicated in, but not limited by, those listed in the introduction to this specification.

The APR profile can be used to devise an APR Alert State, as indicated but not limited to the manner we have previously described. The APR may additionally or alternatively be collected into a nomogram and deviations from the nomogram can be used to monitor recovery. The APR Alert state can be calculated in during the recovery pathway. The APR may be used to trigger a clinical assessment and intervention. The APR Alert trends may then be used as a companion diagnostic for an intervention. APR profiles and alerts can be refined by complications set for a given procedure to produce Bayesian predictions of complications based on large-scale prevalence analysis and profiling. APR profiles can be refined by procedure eg colorectal surgery, urological surgery, pneumonia, acute appendicitis etc. APR profiles may optionally be stratified for patient co-morbidities.

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. A method for treating a patient following a surgical procedure, the method comprising:
    inputting acute phase response (APR) biomarker data defining a level of an acute phase response (APR) biomarker in said patient at a succession of biomarker measurement times following said medical procedure, said APR biomarker data defining a biomarker time course representing an evolution over time of said acute phase response;
    processing said APR biomarker data to determine a derivative with respect to time of said time course from said APR biomarker data to provide APR time series data, wherein said processing of said APR biomarker data to determine said derivative with respect to time of said time course further comprises correcting for a clearance rate of said biomarker in said patient;
    identifying one or both of a maximum and a minimum in said APR time series data;
    determining a value for an alert state variable responsive to said APR time series data; and
    if the alert state variable has a first value then treating the patient for infection.

2. A method as claimed in claim 1 further comprising one or both of disregarding a data value and flagging an error, where said determined derivative has a value defining a rate of fall of said level of said APR biomarker greater than said clearance rate.

3. A method as claimed in claim 1 wherein said determining of said value for said alert state variable comprises identifying one or more of the following conditions:
    (i) a falling level of said APR time series data after an initial delay time;
    (ii) a point of inflection in said APR time series data;
    (iii) a minimum in said APR time series data;
    (iv) a rise in said APR time series data in response to a said biomarker measurement; and
    (v) a fall in the APR time series data in response to a said biomarker measurement;
    and, responsive to said identifying, adjusting said value for said alert state variable.

4. A method as claimed in claim 1 wherein determining if the alert state variable has a first value comprises determining, given said value of said alert state variable, a probability of one of a set of possible patient responses, the set of possible responses including infection.

5. A method as claimed in claim 4 wherein determining if the alert state variable has a first value comprises determining the probability P(response|alert state variable) of a said response given said value of said alert state variable, comprises determining as a function of time:

P(alert state variable|response)·P(alert state variable)

where P(alert state variable|response) is a probability of said alert state variable given said response, and P(alert state variable) is a prior probability of said alert state variable.

6. A method as recited in claim 5 wherein one or more terms of P(alert state variable|response)·P(alert state variable) is dependent upon a comorbidity of said patient.

7. A method as recited in claim 1 wherein said processing of said APR biomarker data comprises evaluating:

$$ARP(t) = \frac{dCRP(t)}{dt} + k_C$$

where APR(t) defines said APR time series data, CRP(t) is defined by said APR biomarker data, and $k_C$ defines said clearance rate of CRP.

8. A method as recited in claim 1 further comprising performing an assay to determine said level of said CRP.

9. A physical data carrier carrying computer program code to implement the method of claim 1.

10. A method as claimed in claim 1 further comprising:
    if the alert state variable has a second value then identifying the patient as suitable for discharge.

11. A method as claimed in claim 1 wherein said APR biomarker comprises CRP (C-Reactive Protein) and said APR biomarker data defines a level of CRP in the patient.

12. A medical system for treating a patient following a surgical procedure, the system comprising:
    working memory;
    program memory;
    a processor coupled to said working memory and to said program memory;
    an input to receive APR biomarker data comprising data representing a level of an acute phase response (APR) biomarker in said patient at a succession of biomarker measurement times following said medical procedure, said APR biomarker data defining a biomarker time course representing an evolution over time of said acute phase response, said APR biomarker comprising CRP (C-Reactive Protein) and said APR biomarker data defining a level of CRP in the patient; and
    wherein said program memory stores processor control code to:
    process said APR biomarker data to determine a derivative with respect to time of said time course from said APR biomarker data to provide APR time series data, wherein said processing of said APR biomarker data to determine said derivative with respect to time of said time course further comprises correcting for a clearance rate of CRP in said patient;
    identify one or both of a maximum and a minimum in said APR time series data;
    determine a value for an alert state variable responsive to said APR time series data; and
    if the alert state variable has a first value then identify the patient for treatment for infection.

* * * * *